US007256280B2

(12) United States Patent
Gordon-Kamm et al.

(10) Patent No.: US 7,256,280 B2
(45) Date of Patent: Aug. 14, 2007

(54) CELL CYCLE NUCLEIC ACIDS, POLYPEPTIDES AND USES THEREOF

(75) Inventors: William J. Gordon-Kamm, Urbandale, IA (US); Keith S. Lowe, Johnston, IA (US); Brian A. Larkins, Tucson, AZ (US); Brian R. Dilkes, Tucson, AZ (US); Yuejin Sun, Westfield, IN (US)

(73) Assignees: Pioneer Hi-Bred International, Inc., Johnston, IA (US); Arizona Board of Regents on Behalf of the University of Arizona, Tucson, AZ (US)

( * ) Notice: Subject to any disclaimer, the term of this patent is extended or adjusted under 35 U.S.C. 154(b) by 9 days.

(21) Appl. No.: 09/993,808

(22) Filed: Nov. 6, 2001

(65) Prior Publication Data

US 2004/0003433 A1    Jan. 1, 2004

Related U.S. Application Data

(60) Provisional application No. 60/246,349, filed on Nov. 7, 2000.

(51) Int. Cl.
C12N 15/82    (2006.01)
C12N 15/29    (2006.01)
A01H 5/00     (2006.01)
A01H 5/10     (2006.01)

(52) U.S. Cl. ............... 536/23.6; 435/320.1; 435/252.3; 435/254.11; 435/348; 435/419; 800/298; 800/320.1; 800/312; 800/322; 800/320; 800/306; 800/320.3; 800/314; 800/320.2

(58) Field of Classification Search ............ 435/252.3, 435/320.1, 419, 468; 536/23.6; 800/290, 800/298
See application file for complete search history.

(56) References Cited

U.S. PATENT DOCUMENTS 4,801,340 A * 1/1989 Inoue et al. ................. 148/103
5,968,821 A   10/1999 Beach et al. ................ 435/325

FOREIGN PATENT DOCUMENTS

| CA | 2329684 | 12/1999 |
|----|---------|---------|
| WO | WO 94/10300 | 5/1994 |
| WO | WO 97/12060 | 4/1997 |
| WO | WO 97/16447 | 5/1997 |
| WO | WO 97/26327 | 7/1997 |
| WO | WO 98/37212 | 8/1998 |
| WO | WO 99/06540 | 2/1999 |
| WO | WO 99/13083 | 3/1999 |
| WO | WO 99/14331 | 3/1999 |
| WO | WO 00/60087 | * 10/2000 |

OTHER PUBLICATIONS

Barcelo P et al. Transgenic cereal (tritordeum) plants obtained at high efficiency by microprojectile bombardment of inflorescence tissue. Plant J. Apr. 1994;5(4):583-92.*

Klein et al. Geneseq Accession No. AAA95281, Jan. 17, 2001, corn cyclin-dependent kinase inhibitor coding sequence #3.*
Klein et al. Geneseq Accession No. AAA95280, Jan. 17, 2001, corn cyclin-dependent kinase inhibitor coding sequence #2.*
Klein et al. Geneseq Accession No. AAA95276, Jan. 17, 2001, corn cyclin-dependent kinase inhibitor coding sequence #1.*
Broun P et al. (Catalytic plasticity of fatty acid modification enzymes underlying chemical diversity of plant lipids. Science. Nov. 13, 1998;282(5392):1315-7.*
Zhou Y et al. The plant cyclin-dependent kinase inhibitor ICK1 has distinct functional domains for in vivo kinase inhibition, protein instability and nuclear localization.Plant J. Aug. 2003;35(4):476-89.*
Sandler et al. Inhibition Of Gene Expression in Transformed Plants By Antisense RNA. Plant Molecular Biology, 1988, vol. 11, No. 3, pp. 301-310.*
van der Krol AR et al. Inhibition of flower pigmentation by antisense CHS genes: promoter and minimal sequence requirements for the antisense effect. Plant Mol Biol. Apr. 1990;14(4):457-66.*
Waterhouse PM et al. Virus resistance and gene silencing: killing the messenger. Trends in Plant Science, Nov. 1999, Vo 4, No. 11, pp. 452-457.*
Sheehy R.E. Reduction of Polygalacturonase Activity in Tomato Fruit by Antisense RNA. Proceedings of the National Academy of Sciences of the United States of America, vol. 85, No. 23. (Dec. 1, 1988), pp. 8805-8809.*
Cayrol et al., "p21 binding to a PCNA causes G1 and G2 cell cycle arrest in p53-deficient cells", *Oncogene* 16:311-310 (1998).
Grafi et al., "Endoreduplication in Maize Endosperm: Involvement of M Phase-Promoting Factor Inhibition and Induction of S Phase-Related Kinases", *Science* 269:1262-1264 (1995).
Hengst et al., "A cell cycle-regulated inhibitor of cyclin-dependent kinases", *Proc. Natl. Acad. Sci. USA* 91:5291-5295 (1994).
Lui et al., "The *Arabidopsis* Cdc2a-interacting protein ICK2 is structurally related to ICK1 and is a potent inhibitor of cyclin-dependent kinase activity in vitro", *The Plant Journal* 21(4):379-385 (2000).
Peter et al., "Joining the Complex: Cyclin-Dependent Kinase Inhibitory Proteins and the Cell Cycle", *Cell* 79:181-184 (1994).
Wang et al., "A plant cyclin-dependent kinase inhibitor gene", *Nature* 386:451-452 (1997).
Wang et al., "ICK1, a cyclin-dependent protein kinase inhibitor from *Arabidopsis thaliana* interacts with both Cdc2a and CycD3, and its expression is induced by abscisic acid", *The Plant Journal* 15(4):501-510 (1998).

(Continued)

*Primary Examiner*—Cynthia Collins

(57) ABSTRACT

The invention provides isolated nucleic acids and their encoded proteins that are involved in cell cycle regulation. The invention further provides recombinant expression cassettes, host cells, transgenic plants, and antibody compositions. The present invention provides methods and compositions relating to altering cell cycle protein content, cell cycle progression, cell number and/or composition of plants.

19 Claims, No Drawings

OTHER PUBLICATIONS

Buell et al., *GenBank Accession No. AC069145, Oryza sativa* chromosome 10 BAC OSJNBb0094K03 genomic sequence (2000).

Fountain et al., Isolation of a cDNA Encoding a G1-Cyclin-Dependent Kinase Inhibitor from Suspension-Cultured Photoautotrophic *Chenopodium rubrum* Cells (Accession No. AJ002173) (PGR 99-057) *Plant Physiol.* 120:339.

Kakimoto, T., DDBJ/EMBL/*GenBank Accession* No. D87545, "CKI1, a histidine kinase homolog implicated in cytokinin signal transduction" (1999).

GCG:Gap Analysis—protein level.

GCG:DNA Gap Analysis -DNA level.

Wang et al., Expression of the plant cyclin-dependent kinase inhibitor ICK1 affects cell division, plant growth and morphology, The Plant Journal 24(5):613-623, 2000.

Buell et al., NCBI Database Accession No. AC069145, *Oryza sativa* chromosome 10 BAC OSJNBb0094K03 genomic sequence (2000).

Buell et al., NCBI Database Accession No. AAG16867, Putative cyclin-dependent kinase inhibitor (2000).

Fountain et al., Isolation of a cDNA Encoding a G1-Cyclin-Dependent Kinase Inhibitor (ICDK) from Suspension Cultured Photoautotrophic *Chenopodium rubrum* L. Cells (Accession No. AJ002173), Plant Gene Register PGR99-057 (1999).

Fountain et al., NCBI Database Accession No. CFJ002173, *Chenopodium rubrum* G1 cyclin-dependent kinase inhibitor mRNA (1999).

Sato et al., EMBL Database Accession No. Q9LRY0, Similarity to cyclin-dependent kinase inhibitor protein (Cyclin-dependent kinase inhibitor 5) (2000).

Larkins et al., Investing the hows and whys of DNA endoreduplication, Journal of Experimental Botany 52(355):183-192 (2001).

* cited by examiner

CELL CYCLE NUCLEIC ACIDS, POLYPEPTIDES AND USES THEREOF

This application claims benefit of priority of co-pending U.S. Provisional Patent Application No. 60/246,349, filed Nov. 7, 2000, which is incorporated by reference herein.

STATEMENT REGARDING FEDERALLY SPONSORED RESEARCH OR DEVELOPMENT

This invention was made with Government support under Contract No. DE-FG03-95ER20183 awarded by the Department of Energy. The Government has certain rights in this invention.

TECHNICAL FIELD

The present invention relates generally to plant molecular biology. More specifically, it relates to nucleic acids and methods for modulating their expression in plants.

BACKGROUND OF THE INVENTION

Cell division plays a crucial role during all phases of plant development. The continuation of organogenesis and growth responses to a changing environment requires precise spatial, temporal and developmental regulation of cell division activity in meristems (and in cells with the capability to form new meristems such as in lateral root formation). Such control of cell division is also important in organs themselves (i.e. separate from meristems per se), for example, in leaf expansion, secondary growth, and endoreduplication.

A complex network controls cell proliferation in eukaryotes. Various regulatory pathways communicate environmental constraints, such as nutrient availability, mitogenic signals such as growth factors or hormones, or developmental cues such as the transition from vegetative to reproductive stages. Ultimately, these regulatory pathways control the timing, frequency (rate), plane and position of cell divisions.

Plants have unique developmental features that distinguish them from other eukaryotes. Plant cells do not migrate, and thus only cell division, expansion and programmed cell death determine morphogenesis. Organs are formed throughout the entire life span of the plant from specialized regions called meristems. In addition, many differentiated cells have the potential to both differentiate and to reenter the cell cycle. There are also numerous examples of plant cell types that undergo endoreduplication, a process involving nuclear multiplication without cytokinesis. The study of plant cell cycle control genes is expected to contribute to the understanding of these unique phenomena. O. Shaul et al., *Regulation of Cell Division in Arabidopsis, Critical Reviews in Plant Sciences,* 15 (2):97-112 (1996).

Current transformation technology provides an opportunity to engineer plants with desired traits. Major advances in plant transformation have occurred over the last few years. However, in many major crop plants, serious genotype limitations still exist. Transformation of some agronomically important crop plants continues to be both difficult and time consuming. For example, it is difficult to obtain a culture response from some maize varieties. Typically, a suitable culture response has been obtained by optimizing medium components and/or explant material and source. This has led to success in some genotypes. While, transformation of model genotypes is efficient, the process of introgressing transgenes into production inbreds is laborious, expensive and time consuming. It would save considerable time and money if genes could be introduced into and evaluated directly in commercial hybrids.

There is evidence to suggest that cells must be dividing for transformation to occur. It has also been observed that dividing cells represent only a fraction of cells that transiently express a transgene. Furthermore, the presence of damaged DNA in non-plant systems (similar to DNA introduced by particle gun or other physical means) has been well documented to rapidly induce cell cycle arrest (W. Siede, *Cell cycle arrest in response to DNA damage: lessons from yeast, Mutation Res.* 337 (2:73-84) 1995. Methods for increasing the number of dividing cells would therefore provide valuable tools for increasing transformation efficiency.

Current methods for genetic engineering in maize require a specific cell type as the recipient of new DNA. These cells are found in relatively undifferentiated, rapidly growing callus cells or on the scutellar surface of the immature embryo (which gives rise to callus). Irrespective of the delivery method currently used, DNA is introduced into literally thousands of cells, yet transformants are recovered at frequencies of $10^{-5}$ relative to transiently-expressing cells. Exacerbating this problem, the trauma that accompanies DNA introduction directs recipient cells into cell cycle arrest and accumulating evidence suggests that many of these cells are directed into apoptosis or programmed cell death. (Reference Bowen et al., Tucson International Mol. Biol. Meetings). Therefore it would be desirable to provide improved methods capable of increasing transformation efficiency in a number of cell types.

In spite of increases in yield and harvested area worldwide, it is predicted that over the next ten years, meeting the demand for corn will require an additional 20% increase over current production (Dowswell, C. R., Paliwal, R. L., Cantrell, R. P. 1996. Maize in the Third World, Westview Press, Boulder, Colo.).

The components most often associated with maize productivity are grain yield or whole-plant harvest for animal feed (in the forms of silage, fodder, or stover). Thus the relative growth of the vegetative or reproductive organs might be selected depending on the ultimate use of the crop. Whether the whole plant or the ear are harvested, overall yield will depend strongly on vigor and growth rate. It would therefore be valuable to develop new methods that contribute to the increase in crop yield.

SUMMARY OF THE INVENTION

It is an object of the present invention to provide nucleic acids and polypeptides relating to the control of cell division, that can be used to identify interacting proteins involved in cell cycle regulation, transgenic plants comprising the nucleic acids and methods for modulating, in a transgenic plant, the expression of the nucleic acids of the present invention.

DETAILED DESCRIPTION OF THE INVENTION

Sequence ID No. 1-CDK_B nucleotide sequence
Sequence ID No. 2-CDK_B polypeptide sequence
Sequence ID No. 3-CDK_C nucleotide sequence
Sequence ID No. 4-CDK_C polypeptide sequence
Sequence ID No. 5-CDK_D nucleotide sequence
Sequence ID No. 6-CDK_D polypeptide sequence Cell cycle transitions in multicellular eukaryotes are mediated by cyclin-dependent kinase (CDK) complexes (Nasmyth, 1993) which contain at least a catalytic subunit and a regulatory subunit. Progression through the cell cycle is, in part, determined by cyclins; regulatory subunits that are structurally related but are specific for each phase of the cycle. Another regulatory subunit is a protein that inhibits CDK activity, a cyclin-dependent kinase inhibitor (CKI) which binds to and inhibits the CDK complex by inhibiting its activity toward exogenous substrates. CKI interferes with CDK activation without modifying the CDK complex.

Progression through the cell cycle may be controlled through modulating the activity of CDK by means of modulating CKI expression and/or activity. Based upon results in other eukaryotes, CKI expression and/or activity should block the G1/S transition and prevent cell division by binding the CDK complex. Perturbation of the cell cycle through modulation of CKI may result in abnormal phenotypes such as changes in cell size, growth, and developmental programs.

Definitions

The term "isolated" refers to material, such as a nucleic acid or a protein, which is: (1) substantially or essentially free from components which normally accompany or interact with it as found in its natural environment. The isolated material optionally comprises material not found with the material in its natural environment; or (2) if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods, or if it is transcribed from DNA which has been altered or produced by non-natural, synthetic methods. The isolated nucleic acid may also be produced by the synthetic re-arrangement ("shuffling") of a part or parts of one or more allelic forms of the gene of interest. Likewise, a naturally-occurring nucleic acid (e.g., a promoter) becomes isolated if it is introduced to a different locus of the genome. Nucleic acids which are "isolated," as defined herein, are also referred to as "heterologous" nucleic acids.

As used herein, "polypeptide" means proteins, protein fragments, modified proteins, amino acid sequences and synthetic amino acid sequences. The polypeptide can be glycosylated or not.

As used herein, "plant" includes but is not limited to plant cells, plant tissue, plant organs, plant pieces and plant seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Preferably fragments of a nucleotide sequence may encode protein fragments that retain the biological activity of the native nucleic acid. However, fragments of a nucleotide sequence which are useful as hybridization probes generally do not encode fragment proteins retaining biological activity. Fragments of a nucleotide sequence are generally greater than 10 nucleotides, preferably at least 20 nucleotides and up to the entire nucleotide sequence encoding the proteins of the invention. Generally probes are less than 1000 nucleotides and preferably less than 500 nucleotides. Fragments of the invention include antisense sequences used to decrease expression of the inventive nucleic acids. Such antisense fragments may vary in length ranging from at least about 20 nucleotides, about 50 nucleotides, about 100 nucleotides, up to and including the entire coding sequence.

By "supression" is intended reduction in expression of a cellular gene product that may be attained upon introduction into the cell of a nucleic acid fragment that is ultimately transcribed to yield a mRNA transcript substantially homologous to a portion of the transcript of the gene of interest.

By "functional fragment" is intended a portion of the nucleotide sequence or a portion of the amino acid sequence and hence protein encoded thereby, characterized by their ability, upon introduction to cells, to affect the G1 to S-phase transition. A functional fragment of a cell cycle gene, such as CDK, is manifested by increased DNA replication in a population of cells and by increased cell division rates. A functional fragment of a cell cycle inhibitor gene, such as CKI, is manifested by decreased DNA replication in a population of cells and by decreased cell division rates.

By "variants" is intended substantially similar sequences. Generally, nucleic acid sequence variants of the invention will have at least 50%, 60%, 70%, or 80%, alternatively at least 85%, 87% or 90% and alternatively at least 92%, 94%, 96%, 98%, or 99% sequence identity to the native nucleotide sequence.

Generally, polypeptide sequence variants of the invention will have at least 50%, 60%, 70%, or 80%, alternatively at least 85%, 87% or 90% and alternatively at least 92%, 94%, 96%, 98%, or 99% sequence identity to the native protein.

As used herein, "sequence identity" or "identity" in the context of two nucleic acid or polypeptide sequences includes reference to the residues in the two sequences that are the same when aligned for maximum correspondence over a specified comparison window. An indication that two peptide sequences are substantially identical is that one peptide is immunologically reactive with antibodies raised against the second peptide. A polypeptide is substantially identical to a second polypeptide, for example, where the two polypeptides differ only by a conservative substitution. Generally, sequence identity of the invention is at least 50%, 60%, 70%, or 80%, alternatively at least 85%, 87% or 90% and alternatively at least 92%, 94%, 96%, 98%, or 99% sequence identity to the native protein or nucleotide.

Methods of alignment of sequences for comparison and determination of "sequence identity" are well-known in the art. For purposes of defining the present invention, the BLAST 2.0 suite of programs using default parameters is used. Altschul et al., *Nucleic Acids Res.* 25:3389-3402 (1997). Software for performing BLAST analyses is publicly available, e.g., through the National Center for Biotechnology Information (http://www.ncbi.nlm.nih.gov/).

By "functionally equivalent" is intended that the sequence of the variant defines a chain that produces a protein having substantially the same biological effect as the native protein of interest. The variant is catalytically active.

By "modulate" is intended to increase, decrease, influence or change.

By "cataytically active" is intended the ability of a protein to bind to retinoblastoma (Rb) or is involved in stimulating DNA replication during the cell cycle.

By "interactor" is intended genes, proteins, polypeptide fragments, antibodies, pharmaceuticals, chemicals, aptamers and peptides capable of modulating expression or activity.

Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. In one embodiment the monocot is corn, sorghum, barley, wheat, millet, or rice. Dicots include soybeans, sunflower, canola, alfalfa, cotton, potato, oil-seed *Brassica* or cassava.

Functional fragments included in the invention can be obtained using primers that selectively hybridize under stringent conditions. Fragments can be made through site directed mutagenesis, restriction, change, DNA shuffling or a variety of methods known in the art. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis and then tested for catalytic activity.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3-8.5.9. Also, see generally, McPherson (ed.), *DIRECTED MUTAGENESIS: A Practical approach*, (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences. Such changes will alter, add or delete a single amino acid or a small percentage of amino acids in the encoded sequence. Variants are referred to as "conservatively modified variants" where the alteration results in the substitution of an amino acid with a chemically similar amino acid. When the nucleic acid is prepared or altered synthetically, advantage can be taken of known codon preferences of the intended host.

The present invention also includes "shufflents" produced by sequence shuffling of the inventive polynucleotides to obtain a desired characteristic. Sequence shuffling is described in PCT publication No. 96/19256. See also, Zhang, J.-H., et al. *Proc. Natl. Acad. Sci. USA* 94:4504-4509 (1997).

The present invention also includes the use of 5' and/or 3' UTR regions for modulation of translation of heterologous coding sequences. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)).

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387-395 (1984)) or MacVector 4.1 (Eastman Kodak Co., New Haven, Conn.).

ESTs encoding CKI can be identified by conducting BLAST (Basic Local Alignment Search Tool; Altschul, S. F., et al., (1993) J. Mol. Biol. 215:403-410; see also www.ncbi.nlm.nih.gov/BLAST/) searches for similarity to sequences contained in the BLAST "nr" database (comprising all nonredundant GenBank CDS translations, sequences derived from the 3-dimensional structure Brookhaven Protein Data Bann:, the last major release of the SWISS-PROT protein sequence database, EMBL, and DDBJ databases). The cDNA sequences can be analyzed for similarity to all publicly available DNA sequences contained in the "nr," database using the BLASTN algorithm provided by the National Center for Biotechnology Information NCBI). The DNA sequences can be translated in all reading frames and compared for similarity to all publicly available protein sequences contained in the "nr" database using the BLASTX algorithm (Gish, W. and States, D. J. (1993) *Nature Genetics* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

For example, the inventive nucleic acids can be optimized for enhanced or suppressed expression in organisms of interest. See, for example, EPA0359472; WO91/16432; Perlak et al. (1991) *Proc. Natl. Acad. Sci. USA* 88:3324-3328; and Murray et al. (1989) *Nucleic Acids Res.* 17:477-498. In this manner, the genes can be synthesized utilizing species-preferred codons. See, for example, Murray et al. (1989) *Nucleic Acids Res.* 17:477-498, the disclosure of which is incorporated herein by reference.

The present invention provides subsequences comprising isolated nucleic acids containing at least 16 contiguous bases of the inventive sequences. For example the isolated nucleic acid includes those comprising at least 20, 25, 30, 40, 50, 60, 75 or 100 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391 and 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics*, 37:327-336 (1996). Other methods for producing full-length libraries are known in the art. See, e.g., Edery et al., *Mol. Cell Biol.* 15 (6):3363-3371 (1995); and PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.* 18 (19):5705-5711 (1990); Patanjali et al., *Proc. Natl. Acad. U.S.A.* 88:1943-1947 (1991); U.S. Pat. Nos. 5,482,685 and 5,637,685; and Soares et al., *Proc. Natl. Acad. Sci. USA* 91:9228-9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, *Technique* 3(2):58-63 (1991); Sive and St. John, *Nucl. Acids Res.* 16 (22):10937 (1988); *Current Protocols in Molecular Biology*, Ausubel et al., Eds., Greene Publishing and Wiley-Interscience, New York (1995); and Swaroop et al., *Nucl. Acids Res.* 19 (8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook et al., *Molecular Cloning: A Laboratory Manual*, 2nd Ed., Cold Spring Harbor Laboratory, Vols. 1-3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Preferably the hybridization is conducted under low stringency conditions which include hybridization with a buffer solution of 30% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. More preferably the hybridization is conducted under moderate stringency conditions which include hybridization in 40% formamide, 1 M NaCl, 1% SDS at 37° C., and a wash in 0.5× to 1×SSC at 55° C. Most preferably the hybridization is conducted under high stringency conditions which include hybridization in 50% formamide, 1 M NaCl, 1% SDS at 37° C., and a wash in 0.1×SSC at 60° C. Hybridization and/or wash conditions can be applied for at least 10, 30, 60, 90, 120, or 240 minutes. Hybridization is typically conducted for 4-6 hours.

An extensive guide to the hybridization of nucleic acids is found in Tijssen, *Laboratory Techniques in Biochemistry and Molecular Biology—Hybridization with Nucleic Acid Probes*, Part I, Chapter 2 "*Overview of principles of hybridization and the strategy of nucleic acid probe assays*", Elsevier, New York (1993); and *Current Protocols in Molecular Biology*, Chapter 2, Ausubel et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and,

*PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22 (3): 481-486 (1997).

In one aspect of the invention, nucleic acids can be amplified from a *Zea mays* library, or a library generally constructed from nuclear transcripts at any stage of intron processing.

Libraries can be made from a variety of maize tissues. Good results have been obtained using mitotically active tissues such as shoot meristems, shoot meristem cultures, embryos, callus and suspension cultures, immature ears and tassels, and young seedlings. The cDNA of the present invention was obtained from developing endosperm. Since cell cycle proteins are typically expressed at specific cell cycle stages it may be possible to enrich for such rare messages using exemplary cell cycle inhibitors such as aphidicolin, hydroxyurea, mimosine, and double-phosphate starvation methods to block cells at the G1/S boundary. Cells can also be blocked at this stage using the double phosphate starvation method. Hormone treatments that stimulate cell division, for example cytokinin, would also increase expression of the cell cycle RNA.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.). and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90-99 (1979); the phosphodiester method of Brown et al., *Meth. Enzymol.* 68:109-151 (1979); the diethylphosphoramidite method of Beaucage et al., *Tetra. Lett.* 22:1859-1862 (1981); the solid phase phosphoramidite triester method described by Beaucage and Caruthers, *Tetra. Letts.* 22 (20):1859-1862 (1981), e.g., using an automated synthesizer, e.g., as described in Needham-VanDevanter et al., *Nucleic Acids Res.* 12:6159-6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

EXPRESSION CASSETTES

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant, bacterial or yeast hosts.

The construction of expression cassettes that can be employed in conjunction with the present invention is well known to those of skill in the art in light of the present disclosure. See, e.g., Sambrook et al., *Molecular Cloning: A Laboratory Manual*; Cold Spring Harbor, New York; (1989); Gelvin et al., *Plant Molecular Biology Manual*; (1990); *Plant Biotechnology: Commercial Prospects and Problems*, eds. Prakash et al.; Oxford & IBH Publishing Co.; New Delhi, India; (1993); and Heslot et al.; *Molecular Biology and Genetic Engineering of Yeasts*; CRC Press, Inc., USA; (1992); each incorporated herein in its entirety by reference. For example, plant expression vectors may include (1) a cloned plant nucleic acid under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promote, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47:95-102 (1986), and Reina, M., Ponte, I., Guillen, P., Boronat, A. and Palau, J., Sequence analysis of a genomic clone encoding a Zc2 protein from *Zea mays* W64 A, *Nucleic Acids Res.* 18 (21):6426 (1990). See the following site relating to the waxy promoter: Kloesgen, R. B., Gierl, A., Schwarz-Sommer, Z S. and Saedler, H., Molecular analysis of the waxy locus of *Zea mays, Mol. Gen. Genet.* 203:237-244 (1986). Promoters that express in the embryo, pericarp, and endosperm are disclosed in WO00/11177 and WO00/12733. The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, Mol. Cell Biol. 8:4395-4405 (1988); Callis et al., Genes Dev. 1:1183-1200 (1987). Use of maize introns Adh1-S intron 1, 2, and 6, the Bronze-1 intron are known in the art. See generally, The Maize Handbook, Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of *Agrobacterium tumefaciens* described by Rogers et al., Meth. In Enzymol. 153:253-277 (1987). Exemplary *A. tumefaciens* vectors useful herein are plasmids pKYLX6 and pKYLX7 of Schardi et al., Gene 61:1-11 (1987) and Berger et al., Proc. Natl. Acad. Sci. U.S.A. 86:8402-8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., Proc. Nat'l. Acad. Sci. (USA) 85:8805-8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., The Plant Cell 2:279-289 (1990) and U.S. Pat. No. 5,034,323.

A method of down-regulation of the protein involves using PEST sequences that provide a target for degradation of the protein.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., Nucleic Acids Res (1986) 14:4065-4076, describe covalent bonding of a single-stranded DNA fragment with alkylating derivatives of nucleotides complementary to target sequences. A report of similar work by the same group is that by Knorre, D. G., et al., Biochimie (1985) 67:785-789. Iverson and Dervan also showed sequence-specific cleavage of single-stranded DNA mediated by incorporation of a modified nucleotide which was capable of activating cleavage (J Am Chem Soc (1987) 109:1241-1243). Meyer, R. B., et al., J Am Chem Soc (1989) 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., Biochemistry (1988) 27:3197-3203. Use of crosslinking in triple-helix forming probes was also disclosed by Home et al., J Am Chem Soc (1990) 112:2435-2437. Use of N4, N4-ethanocytosine as an alkylating agent to crosslink to single-stranded oligonucleotides has also been described by Webb and Matteucci, J Am Chem Soc (1986) 108:2764-2765; Nucleic Acids Res (1986) 14:7661-7674; Feteritz et al., J. Am. Chem. Soc. 113:4000(1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

PROTEINS

Proteins of the present invention include proteins derived from the native protein by deletion (so-called truncation), and addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology*

(MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be utilized.

In constructing variants of the proteins of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

The isolated proteins of the present invention include a polypeptide comprising at least 23 contiguous amino acids encoded by any one of the nucleic acids of the present invention, or polypeptides which are conservatively modified variants thereof. The proteins of the present invention or variants thereof can comprise any number of contiguous amino acid residues from a polypeptide of the present invention, wherein that number is selected from the group of integers consisting of from 23 to the number of residues in a full-length polypeptide of the present invention. Optionally, this subsequence of contiguous amino acids is at least 25, 30, 35, or 40 amino acids in length, often at least 50, 60, 70, 80, or 90 amino acids in length.

The present invention includes catalytically active polypeptides (i.e., enzymes). Catalytically active polypeptides will generally have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

The present invention includes modifications that can be made to an inventive protein without diminishing its biological/catalytic activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A protein of the present invention can be expressed in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the nucleic acid of interest can be isolated in significant quantities for introduction into the desired plant cells.

Host cells that can be used in the practice of this invention include prokaryotes, including bacterial hosts such as *Eschericia coli, Salmonella typhimurium*, and *Serratia marcescens*. Eukaryotic hosts such as yeast or filamentous fungi may also be used in this invention. One embodiment is to plant promoters that do not cause expression of the polypeptide in bacteria.

Commonly used prokaryotic control sequences include promoters such as the beta lactamase (penicillinase) and lactose (lac) promoter systems (Chang et al., *Nature* 198: 1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus* sp. and *Salmonella* (Palva et al., *Gene* 22:229-235 (1983); Mosbach et al., *Nature* 302:543-545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in *The Peptides: Analysis, Synthesis, Biology. Vol. 2: Special Methods in Peptide Synthesis, Part A.*; Merrifield et al., *J. Am. Chem. Soc.* 85: 2149-2156 (1963), and Stewart et al., *Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) is known to those of skill.

The proteins of this invention may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation of the polypeptides can be effected by increasing or decreasing the concentration and/or the composition of the polypeptides in a plant. The method comprises transforming a plant cell with an expression cassette comprising a polynucleotide of the present invention to obtain a transformed plant cell, growing the transformed plant cell under plant forming conditions, and inducing expression of the polynucleotide in the plant for a time sufficient to modulate concentration and/or composition of the polypeptides in the plant or plant part.

In one embodiment of the present invention, cell cycle gene expression could increase or decrease cell growth. It could also increase or decrease cell division, alter the percentage of time that cells of the plant are arrested or change the amount of time in a particular portion of the cell cycle. Expression of cell cycle genes can increase growth and growth rate, increase plant height and or size and also increase crop yield. It can also provide a positive growth advantage and can enhance or inhibit organ growth (e.g. seed, root, shoot, ear, tassel, stalk, pollen, stamen (male sterility), parthenocarpic fruits, organ oblation). Cell cycle gene expression can increase transformation efficiency, enhance embryogenic response (size and growth rate), increase induction of callus, provide a positive selection method, use of co-transformation, and increase plant regeneration. Expression of cell cycle genes can increase the number of pods/plant, increase seeds/pod, and alter lag time in seed development. It can improve response to environmental stress (e.g. drought, heat, cold) and provide hormone independent growth. Expression of cell cycle genes can be altered and all or portions of genes removed using FLP/FRT, PEST, altered PEST sequence, Rb binding site, or the cyclin box. Patterns of expression can also be altered by using a variety of promoters including inducible promoters (e.g. inducible chemically, hormonally in, tissue specific). Expression of cell cycle genes can be in planta or in vitro. For example, cell cycle gene expression in bioreactors can increase growth rate and production of protein or other products.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868.

In particular, modulating cell cycle proteins are expected to provide a positive growth advantage and increase crop yield. Cell cycle nucleic acids can be adducted to a second nucleic acid sequence encoding a DNA-binding domain, for use in two-hybrid systems to identify CKI-interacting proteins. It is expected that modulating the level of cell cycle protein, i.e. overexpression of CKI will increase endoreduplication. Endoreduplication is expected to increase the size of the seed, the size of the endosperm and the amount of protein in the seed.

Also, modulating cell cycle proteins affects the cell number in a tissue of a plant, thereby affecting the size and characteristics of that tissue organ. Modulation could affect any plant tissue such as, but not limited to root, seed, tassel, ear, silk, stalk, embryo, flower, grain, germ, head, leave, stem, seed, trunk, meristem or fruit. Changes in plant tissue will influence quality traits, agronomic traits and susceptibility to disease and insects.

In some embodiments, an isolated nucleic acid (e.g., a vector) comprising a promoter sequence is transfected into a plant cell. Subsequently, a plant cell comprising the isolated nucleic acid is selected for by means known to those of skill in the art such as, but not limited to, Southern blot, DNA sequencing, or PCR analysis using primers specific to the promoter and to the nucleic acid and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration of the polypeptides is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development.

Modulating nucleic acid expression temporally and/or in particular tissues can be controlled by employing the appropriate promoter operably linked to a polynucleotide of the present invention in, for example, sense or antisense orientation as discussed in greater detail above. Induction of expression of a polynucleotide of the present invention can also be controlled by exogenous administration of an effective amount of inducing compound. Inducible promoters and inducing compounds that activate expression from these promoters are well known in the art.

In one embodiment, the polypeptides of the present invention are modulated in monocots, preferably cereals, or dicots. Plants include corn, soybean, sunflower, sorghum, canola, wheat, alfalfa, cotton, rice, barley, oil-seed *Brassica* or millet. In another embodiment the polypeptides of this present invention are modulated in bacteria and yeast.

Means of detecting the proteins of the present invention are not critical aspects of the present invention. In one embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B. V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and Non-isotopic Immunoassays, Ngo, Ed., Plenum Press, NY (1988).

Typical methods for detecting proteins include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256:495-497 (1975).

Other suitable techniques involve selection of libraries of recombinant antibodies in phage or similar vectors (see, e.g., Huse et al., *Science* 246:1275-1281 (1989); and Ward et al., *Nature* 341:544-546 (1989); and Vaughan et al., *Nature Biotechnology*, 14:309-314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845-851 (1996). Also, recombinant immunoglobulins may be produced. See, Cabilly, U.S. Pat. No. 4,816,567; and Queen et al., *Proc. Nat'l. Acad. Sci.* 86:10029-10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transfection/Transformation of Cells

The method of transformation/transfection is not critical to the invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide of the present invention, for example a cDNA, RNA or a genomic sequence, will be used to construct an expression cassette that can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weisinger et al., *Ann. Rev. Genet.* 22:421-477 (1988). For example, the DNA construct may be introduced directly into the genomic DNA of the plant cell using techniques such as electroporation, PEG-mediated transfection, particle bombardment, silicon fiber delivery, or microinjection of plant cell protoplasts or embryogenic callus. See, e.g., Tomes et al., *Direct*

DNA Transfer into Intact Plant Cells Via Microprojectile Bombardment. pp. 197-213 in Plant Cell, Tissue and Organ Culture, Fundamental Methods. eds. O. L. Gamborg and G. C. Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

Also, a combination of particle bombardment and *Agrobacterium* host is found in U.S. Pat. No. 5,932,782.

The introduction of DNA constructs using polyethylene glycol precipitation is described in Paszkowski et al., *Embo J.* 3:2717-2722 (1984). Electroporation techniques are described in Fromm et al., *Proc. Natl. Acad. Sci.* 82: 5824 (1985). Ballistic transformation techniques are described in Klein et al., *Nature* 327:70-73 (1987).

*Agrobacterium tumefaciens*-meditated transformation techniques are well described in the scientific literature. See, for example Horsch et al., *Science* 233:496-498 (1984), and Fraley et al., *Proc. Natl. Acad. Sci.* 80:4803 (1983). For instance, *Agrobacterium* transformation of maize is described in U.S. Pat. No. 5,550,318 and U.S. patent application Ser. No. 08/788,018 filed Jan. 24, 1997.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., *Plant Cell Physiol.* 25:1353, 1984), (3) the vortexing method (see, e.g., Kindle, *Proc. Natl. Acad. Sci., USA* 87:1228, (1990).

DNA can also be introduced into plants by direct DNA transfer into pollen as described by Zhou et al., Methods in Enzymology, 101:433 (1983); D. Hess, Intern Rev. Cytol., 107:367(1987); Luo et al., *Plant Mol. Biol. Reporter* 6:165 (1988). Expression of polypeptide coding nucleic acids can be obtained by injection of the DNA into reproductive organs of a plant as described by Pena et al., Nature, 325:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27-54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For regeneration of maize see, McCormick et al. (1986) *Plant Cell Reports* 5:86-89.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124-176 (1983); and Binding, *Regeneration of Plants, Plant Protoplasts*, CRC Press, Boca Raton, pp. 21-73 (1985).

The regeneration of plants containing the foreign gene introduced by *Agrobacterium* can be achieved as described by Horsch et al., *Science,* 227:1229-1231 (1985) and Fraley et al., *Proc. Natl. Acad. Sci. U.S.A.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467-486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

One embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants that can be used in the method of the invention include monocotyledonous and dicotyledonous plants. Plants include corn, soybean, sunflower, sorghum, canola, wheat, alfalfa, cotton, rice, barley, oil-seed *Brassica* and millet.

Seeds derived from plants regenerated from transformed plant cells, plant parts or plant tissues, or progeny derived from the regenerated transformed plants, may be used directly as feed or food, or further processing may occur.

Expression of the inventive nucleic acids in plants, such as corn is expected to enhance growth and biomass accumulation. Other more specialized applications exist for these nucleic acids at the whole plant level. It has been demonstrated that endoreduplication occurs in numerous cell types within plants, but this is particularly prevalent in maize endosperm, the primary seed storage tissue. Under the direction of endosperm-specific promoters, expression of cell cycle genes (and possibly expression of such genes in conjunction with genes that inhibit mitosis) will further stimulate the process of endoreduplication.

Two Hybrid System

CKI can be used in a two-hybrid system to identify maize genes involved in control of cell division. CKI gene expression plays a prominent role as an antiproliferative agent, inhibiting cell cycle progression. The eukaryotic cell cycle is controlled by the sequential activation and inhibition of a phosphorylation cascade centered around a suite of regulatory kinases called cyclin dependant kinases, and the respective stage-specific cylins that asociate with the CDK's. The onset of mitosis, and the onset and maintenance of S-phase are marked by a high level of CDK activity.

The protein encoded by the CKI gene is a small proteinaceous inhibitor containing a conserved region for binding both the cyclin and p34cdc2 subunits of cyclin dependant kinase. As such, the CKI genes and their encoded proteins can potentially be used to identify other proteins involved in the above processes. This can be done using the CKI gene as bait (the target fused to the DNA-binding domain) in a yeast two-hybrid screen. Methods for two-hybrid library construction, cloning of the reporter gene, cloning of the DNA-binding and activation domain hybrid gene cassettes, yeast culture, and transformation of the yeast are all done according to well-established methods (see Sambrook et al., 1990; Ausubel et al., 1990; Hannon and Bartels, 1995). When maize CKI is used as bait in such a two-hybrid screen, proteins that interact with CKI such as cyclin dependent kinases and cyclins per se are identified.

Transient CKI-Antisense Expression Stimulates Cell Division and Enhances Transgene Integration.

Regardless of the method of DNA delivery, cells competent for the integration of foreign DNA must be actively dividing. There is a growing body of evidence suggesting that integration of foreign DNA occurs in dividing cells (this includes both *Agrobacterium* and direct DNA delivery methods). It has long been observed that dividing transformed cells represent only a fraction of cells that transiently express a transgene. It is well known (in non-plant systems) that the delivery of damaged DNA, (similar to what we introduce by particle gun delivery methods) induces checkpoint controls and inhibits cell cycle progression. Cell cycle blockage is typically regulated by proteins such as CKI. This inhibition can be obviated by transient down-regulation of negative regulators such as CKI. Regardless of the mechanism of arrest; i.e. presence of damaged DNA or delivery into a non-cycling differentiated cell, stimulation of the cell cycle will increase integration frequencies.

Transient CKI-Antisense Expression Stimulates Cell Division and Enhances Transgene Integration Transient expression of the CKI-antisense, or other means of down-regulating CKI, releases the cells to progress through the cell cycle and divide. This effectively overcomes the G1/S checkpoint controls, and increases the proportion of recipient-cells (i.e. into which DNA was introduced) that enter S-phase. This stimulation through the G1/S transition in cells harboring transgenic plasmid DNA, or the corresponding polypeptide, provides an optimal cellular environment for integration of the introduced genes.

Use of Antisense Oligonucleotides Against CKI to Transiently Stimulate Cell Division and Enhances Transgene Integration.

An alternative to conventional antisense strategies is the use of antisense oligonucleotides (often with chemically-modified nucleotides). Such an antisense oligonucleotide, typically a 15-18 mer (but this size can vary either more or less), is designed to bind around accessible regions such as the ribosomal binding site around the "Start" codon. Introduction of the antisense oligonucleotide into a cell will transiently stop expression of the targeted gene.

In cells that receive such an antisense oligonucleotide targeted to CKI, the antisense oligonucleotide transiently disrupts CKI expression and stimulates entry into S-phase (as observed in mammalian cells—see Nuell et al., 1991, *Mol. and Cell. Biology* 11 (3):1372-1381).

Use of Antibodies Raised Against CKI to Transiently Stimulate Cell Division and Enhance Transgene Integration.

Antibodies directed against CKI can also be used to mitigate CKI's cell cycle-inhibitory activity, thus stimulating the cell cycle and transgene integration. Genes encoding single chain antibodies, expressed behind a suitable promoter, for example the ubiquitin promoter, could be used in such a fashion. Transient expression of an anti-CKI antibody could temporarily disrupt normal CKI function (i.e. preventing its repressive binding to the Cyclin-CDK complex) and thus stimulate the cell cycle. Alternatively, antibodies raised against CKI could be purified and used for direct introduction into maize cells.

The methods above represent various means of using the CKI-antisense or anti-CKI antibodies, or antisense oligonucleotides to transiently stimulate DNA replication and cell division, which in turn enhances transgene integration by providing an improved cellular/molecular environment for this event to occur.

Methods are contemplated wherein the CKI nucleic acids, fragments, and/or polypeptides are used to improve transformation.

Altering CKI Expression Stimulates the Cell Cycle and Growth

Based on results in other eukaryotes, expression of the ZmCKI gene should block the G1/S transition and prevent cell division. This decrease in division rate is assessed in a number of different manners, being reflected in larger cell size, less rapid incorporation of radiolabeled nucleotides, and slower growth (i.e. less biomass accumulation). Converesly, expression of CKI antisense (or an appropriate antisense oligonucleotide, or anti-CKI antibody) will result in smaller cells, more rapid incorporation of radiolabeled nucleotides, and faster growth.

Control of CKI-Antisense Expression Using Tissue-Specific or Cell-Specific Promoters Provides a Differential Growth Advantage.

CKI-antisense expression using tissue-specific or cell-specific promoters stimulates cell cycle progression in the expressing tissues or cells. For example, using a seed-specific promoter will stimulate cell division rate and result in increased seed biomass. Alternatively, driving CKI-antisense expression with a strongly-expressed, early, tassel-specific promoter will enhance development of this entire reproductive structure. Expression of CKI antisense in other cell types and/or at different stages of development will similarly stimulate cell division rates.

Meristem Transformation

Meristem transformation protocols rely on the transformation of apical initials or cells that can become apical initials following reorganization due to injury or selective pressure. The progenitors of these apical initials differentiate to form the tissues and organs of the mature plant (i.e. leaves, stems, ears, tassels, etc.). The meristems of most angiosperms are layered with each layer having its own set of initials. Normally in the shoot apex these layers rarely mix. In maize the outer layer of the apical meristem, the L1, differentiates to form the epidermis while descendents of cells in the inner layer, the L2, give rise to internal plant parts including the gametes. The initials in each of these layers are defined solely by position and can be replaced by adjacent cells if they are killed or compromised. Meristem transformation frequently targets a subset of the population of apical initials and the resulting plants are chimeric. If for example, 1 of 4 initials in the L1 layer of the meristem are transformed only ¼ of epidermis would be transformed. Selective pressure can be used to enlarge sectors but this selection must be non-lethal since large groups of cells are required for meristem function and survival.

Transformation of an apical initial with a CKI-antisense sequence under the expression of a promoter active in the apical meristem (either meristem-specific or constitutive) would allow the transformed cells to grow faster and displace wild-type initials driving the meristem towards homogeneity and minimizing the chimeric nature of the plant body.

Transient expression of the CKI-antisense sequence in meristem cells, through stimulation of the G1→S transition, will result in greater integration frequencies and hence more numerous transgenic sectors. Integration and expression of the CKI-antisense sequence will impart a competitive advantage to expressing cells resulting in a progressive enlargement of the transgenic sector. Due to the enhanced growth rate in CKI-antisense-expressing meristem cells, they will supplant wild-type meristem cells as the plant continues to grow. The result will be both enlargement of transgenic sectors within a given cell layer (i.e. periclinal expansion) and into adjacent cell layers (i.e. anticlinal invasions). As cells expressing the CKI-antisense occupy an increasingly large proportion of the meristem, the frequency of transgene germline inheritance goes up accordingly.

Influencing Fertility

Tissue- and temporal-specific gene expression and regulation is found, inter alia, during sexual reproduction in eukaryotes. In plant gametogenesis, important cytological and biochemical changes occur during pollen development when the asymmetric mitotic division of the haploid microspore results in the formation of two cells each with different developmental fates. The vegetative cell supports pollen growth while the generative cell undergoes mitosis and develops into sperm cells. Messenger RNAs specific to both pathways within pollen have been identified in plants such as maize, tomato, tobacco, rice and pansy; and messages specific to pollen or to one or more other cell types within anther such as tapetum, epidermis and stomium have also been identified.

It is envisioned that the use of tissue specific promoters known to those of skill in the art, such as MS45 (WO98/

59061) could limit inducibility to specific tissues or cell types. Additionally, the EcR/USP system (WO00/15791) with tissue specific promoters could limit expression to given sights within an organism and facilitate the targeting of gene expression to just those given sights or developmental stages. The system could thus be used to selectively induce expression in the seed or in the reproductive structures of a plant without expression in other areas of the organism.

An embodiment of particular interest to the inventors is the use of the claimed invention in the promotion of fertility or sterility in mature plants. The inventors envision the use of the system to promote or repress the expression of genes in tissues of plants that facilitate reproduction. One of skill in the art would recognize that specific genes are known that may be selectively induced or expressed in order to regulate the fertility of a given plant. The inventors envision the transformation of plants with CKI genes under the control such promoters. Thus fertility or sterility could be controlled in such a plant through the introduction of the proper ligand. Transgenic plants and plant cells may be transformed to contain two DNA constructs. The first chimeric protein construct would contain a tissue specific promoter, an organism specific transcription activator and an ecdysone receptor specific ligand binding domain. The second chimeric protein construct would contain a response element, a constitutive promoter and a CKI gene. Treatment of a transgenic plant containing this system with ecdysone would lead to expression of the CKI gene and result in infertility.

For certain uses such as hybrid production it may also be desirable to completely eliminate the male or female inflorescence. Expressing CKI at early stages of ear or tassel development will result in failure of these organs to develop.

The present invention will be further described by reference to the following detailed examples. It is understood, however, that there are many extensions, variations, and modifications on the basic theme of the present invention beyond that shown in the examples and description, which are within the spirit and scope of the present invention. All publications, patents, and patent applications cited herein are hereby incorporated by reference.

EXAMPLES

The present invention is further defined in the following Examples, in which all parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Isolation of Maize CKI Genes

Total RNA was isolated from corn tissues with TRIzol Reagent (Life Technology Inc. Gaithersburg, Md.) using a modification of the guanidine isothiocyanate/acid-phenol procedure described by Chomczynski and Sacchi [Chomczynski, P., and Sacchi, N., *Anal. Biochem.* 162, 156 (1987)]. In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation:

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

cDNA Library Construction:

cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites. *Zea mays* tissue from tassel and vegetative meristem was employed.

Sequencing Template Preparation:

Individual colonies were picked and DNA was prepared either by PCR with M13 forward primers and M13 reverse primers, or by plasmid isolation. All the cDNA clones were sequenced using M13 reverse primers (*PROTOCOLS*, Murray (ed.), pages 271-281 (Humana Press, Inc. 1991)).

Example 2

Using CKI in a Two-Hybrid System to Identify Maize Genes Involved in Control of Cell Division The CKI genes and their encoded proteins can be used to identify other proteins involved in the above processes. This can be done using the CKI gene as bait (the target fused to the DNA-binding domain) in a yeast two-hybrid screen. Methods for two-hybrid library construction, cloning of the reporter gene, cloning of the DNA-binding and activation domain hybrid gene cassettes, yeast culture, and transformation of the yeast are all done according to well-established methods (see Sambrook et al., 1990; Ausubel et al., 1990; Hannon and Bartels, 1995). When maize CKI is used as bait in such a two-hybrid screen, proteins that interact with CKI such as cyclin dependent kinases and cyclins per se may be identified.

Example 3

Transient CKI-Antisense Expression Stimulates Cell Division and Enhances Transgene Integration A CKI-antisense sequence is cloned into a cassette with a constitutive promoter (i.e. either a strong maize promoter such as the ubiquitin promoter including the first ubiquitin intron, or a weak constitutive promoter such as nos). Delivery of the CKI-antisense DNA in an appropriate plant expression cassette (for example, in a UBI::ZmCKI-antisense::pinII-containing plasmid) along with UBI::bar::pinII can be accomplished through numerous well-established methods for plant transformation. Using one of these methods, DNA is introduced into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids.

Cytological methods can be used to verify increased frequencies of progression through S-phase and mitosis (i.e. for cells in which a visual marker such as GFP was transformed alongside CKI the green fluorescent cells will exhibit a higher mitotic index). Cells in S-phase (undergoing DNA replication) can be monitored by detecting nucleotide analog incorporation. For example, following incubation of cells with bromodeoxyuridine (BrdU) incorporation of this thymidine analog can be detected by methods such as antiBrdU immunocytochemistry or through enhancement of Topro3 fluorescence following BrdU labeling. CKI expression will increase the proportion of cells incorporating BrdU (i.e. a higher percentage of transformed cells will incorporate BrdU relative to untransformed cells). Increased DNA synthesis can also be monitored using such methods as fluorescence activated cell sorting (FACS) of protoplasts (or nuclei), in conjunction with appropriate BrdU-insensitive fluorescent DNA labels such as propidium iodide and DAPI or BrdU-detecting methods described above. For example, tissue is homogenized to release nuclei that are analyzed using the FACS for both green fluorescence (from our accompanying GFP marker) and DNA content. Such FACS analysis demonstrates that expression of a co-transformed GFP reporter correlates with CKI-induced changes in the ratios of cells in G1, S and G2.

Similar experiments can be run using the fluorescently labeled anti-BrdU antisera to demonstrate that CKI expression increased the percentage of cells in S-phase. Cell cycle stage-specific probes can also be used to monitor cell cycle progression. For example, numerous spindle-associated proteins are expressed during a fairly narrow window during mitosis, and antibodies or nucleic acid probes to cyclins, histones, or DNA synthesis enzymes can be used as positive markers for the G1/S transition. For cells that have received the CKI-antisense gene cassette, stimulation of the cell cycle is manifested in an increased mitotic index, detected by staining for mitotic figures using a DNA dye such as DAPI or Hoechst 33258. FACS analysis of CKI-antisense-expressing cells shows that a high percentage of cells have progressed into or through S-phase. Progression through S-phase will be manifested by fewer cells in G1 and more rapid cycling times (i.e. shorter G1 and G2 stages). A higher percentage of cells are labeled when cell cycle stage-specific probes are used, as mentioned above.

To assess the effect on transgene integration, growth of bialaphos-resistant colonies on selective medium is a reliable assay. Within 1-7 days after DNA introduction, the embryos are moved onto culture medium containing 3 mg/l of the selective agent bialaphos. Embryos, and later callus, are transferred to fresh selection plates every 2 weeks. After 6-8 weeks, transformed calli are recovered. Transgenic callus containing the introduced genes can be verified using PCR and Southern analysis. Northern analysis can also be used to verify which calli are expressing the bar gene, and/or the CKI-antisense construct. In immature embryos that had transient, elevated CKI-antisense expression, higher numbers of stable transformants are recovered (likely a direct result of increased integration frequencies). Increased trangene intregration frequency can also be assessed using such well-established labeling methods such as in situ hybridization.

Sometimes (i.e. using transient CKI-antisense-mediated cell cycle stimulation to increase transient integration frequencies), it is desirable to reduce the likelihood of ectopic stable expression of CKI-antisense. Strategies for transient-only expression can be used. This includes delivery of RNA (transcribed from the CKI-antisense construct) along with the transgene cassettes to be integrated to enhance transgene integration by transient stimulation of cell division. Using well-established methods to produce CKI-antisense-RNA, this can then be purified and introduced into maize cells using physical methods such as microinjection, bombardment, electroporation or silica fiber methods.

Example 4

Use of Antisense Oligonucleotides Against CKI to Transiently Stimulate Cell Division and Enhance Transgene Integration An alternative to conventional antisense strategies is the use of antisense oligonucleotides (often with chemically-modified nucleotides). Such an antisense oligonucleotide, typically a 15-18 mer (but this size can vary either more or less), is designed to bind around accessible regions such as the ribosomal binding site around the "Start" codon. Introduction of the antisense oligonucleotide into a cell will transiently stop expression of the targeted gene. For example, an antisense oligonucleotide of between 15 to 18 nucleotides in length, that is complementary (in reverse orientation) to the sequence surrounding the Start codon of the CKI structural gene, is introduced into maize cells. These methods of introduction for the oligonucleotide are similar to those previously described above for introduction of plasmids. Such a CKI-targeting antisense oligonucleotide will transiently depress CKI expression, and these cells will accordingly be transiently stimulated to progress from the G1 to S phase of the cell cycle. In this manner, cell division is transiently stimulated and transgenic integration during this period is enhanced.

Example 5

Use of Antibodies Raised Against CKI to Transiently Stimulate Cell Division and Enhance Transgene Integration Genes encoding single chain antibodies directed against CKI, expressed behind a suitable promoter, for example the ubiquitin promoter, are introduced into maize cells using physical methods such as microinjection, bombardment, electroporation or silica fiber methods. Alternatively, single chain anti-CKI is delivered from *Agrobacterium tumefaciens* into plant cells in the form of fusions to *Agrobacterium* virulence proteins. Fusions are constructed between the anti-CKI single chain antibody and bacterial virulence proteins such as VirE2, VirD2, or VirF which are known to be delivered directly into plant cells. Fusions are constructed to retain both those properties of bacterial virulence proteins required to mediate delivery into plant cells and the anti-CKI activity required for stimulating cell division and enhancing transgene integration. This method ensures a high frequency of simultaneous co-delivery of T-DNA and functional anti-CKI protein into the same host cell.

Example 6

Altering CKI Expression Stimulates the Cell Cycle and Growth

Delivery of the CKI-antisense in an appropriate plant expression cassette is accomplished through numerous well-established methods for plant cells, including for example particle bombardment, sonication, PEG treatment or electroporation of protoplasts, electroporation of intact tissue, silica-fiber methods, microinjection or *Agrobacterium*-mediated transformation. As an alternative to conventional deliver of bacterial plasmids, introduction of a viral plasmid from which a CKI-antisense sequence is expressed could also be employed.

The result of ZmCKI-antisense expression will be to stimulate the G1/S transition and hence cell division, providing the optimal cellular environment for integration of introduced genes. However, beyond the transient effects on transgenic integration, continued expression of the ZmCKI-antisense will trigger a tissue culture response (cell divisions) in genotypes that typically do not respond to conventional culture techniques, or stimulate growth of transgenic tissue beyond the normal rates observed in wild-type (non-transgenic) tissues. To demonstrate this, the CKI-antisense gene is cloned into a cassette with a constitutive promoter (i.e. either a strong maize promoter such as the ubiquitin promoter including the first ubiquitin intron, or a weak constitutive promoter such as nos). Either particle-mediated DNA delivery or *Agrobacterium*-mediated delivery are used to introduce the UBI::ZmCKIantisense::pinII-containing plasmid along with a UBI::bar:pinII-containing plasmid into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids, and within 1-7 days the embryos are moved onto culture medium containing 3 mg/l of the selective agent bialaphos. Embryos, and later callus, are transferred to fresh selection plates every 2 weeks.

After 6-8 weeks, transformed calli are recovered. In treatments where both the bar gene and CKI-antisense gene have been transformed into immature embryos, a higher number of growing calli are recovered on the selective medium and callus growth is stimulated (relative to treatments with the bar gene alone). When the CKI-antisense gene is introduced without any additional selective marker, transgenic calli can be identified by their ability to grow more rapidly than surrounding wild-type (non-transformed) tissues. Transgenic callus can be verified using PCR and Southern analysis. Northern analysis can also be used to verify which calli are expressing the bar gene, and which are expressing the maize CKI gene at levels above normal wild-type cells (based on hybridization of probes to freshly isolated mRNA population from the cells).

Example 7

Control of CKI-Antisense Expression Using Tissue-Specific or Cell-Specific Promoters Provides a Differential Growth Advantage A ZmCKI-antisense gene is expressed using tissue-specific or cell-specific promoters which stimulates cell cycle progression in the expressing tissues or cells. For example, using a seed-specific promoter will stimulate cell division rate and result in increased seed biomass. Alternatively, driving ZmCKI-antisense expression with a strongly-expressed, early, tassel-specific promoter will enhance development of this entire reproductive structure.

Expression of ZmCKI-antisense genes in other cell types and/or at different stages of development will similarly stimulate cell division rates. Root-specific or root-preferred expression of CycD will result in larger roots and faster growth (i.e. more biomass accumulation).

Example 8

Meristem Transformation

The CKI-antisense sequence is cloned into a cassette with a promoter that is active within the meristem (i.e. either a strong constitutive maize promoter such as the ubiquitin promoter including the first ubiquitin intron, or a promoter active in meristematic cells such as the maize histone, cdc2 or actin promoter). Coleoptilar stage embryos are isolated and plated meristem up on a high sucrose maturation medium (see Lowe et al., 1997, In *Genetic Biotechnology and Breeding of Maize and Sorghum*, A S Tsaftaris, ed., *Royal Society of chemistry*, Cambridge, UK, pp 94-97). The CKI-antisense expression cassette along with a reporter construct such as Ubi:GUS:pinII can then be co-delivered (preferably 24 hours after isolation) into the exposed apical dome using conventional particle gun transformation protocols. As a control the CKI-antisense construct can be replaced with an equivalent amount of pUC plasmid DNA. After a week to 10 days of culture on maturation medium the embryos can be transferred to a low sucrose hormone-free germination medium. Leaves from developing plants can be sacrificed for GUS staining.

Example 9

Use of Flp/Frt System to Excise the CKI-Antisense Cassette

In cases where the CKI-antisense has been integrated and CKI-antisense expression is useful in the recovery of maize trangenics, but is ultimately not desired in the final product, the CKI-antisense expression cassette (or any portion thereof that is flanked by appropriate FRT recombination sequences) can be excised using FLP-mediated recombination (U.S. Pat. No. 5,929,301).

Example 10

Influencing Fertility

It is envisioned that the use of male (e.g. MS45) and female (e.g. nuc1 and LEC1) tissue-preferred promoters known to those of skill in the art, could limit inducibility to specific tissues or cell types. Additionally, the EcR/USP system with tissue specific promoters could limit expression to given sights within an organism and facilitate the targeting of gene expression to just those given sights or developmental stages. The system could thus be used to selectively induce expression in the seed or in the reproductive structures of a plant without expression in other areas of the organism.

A tissue-preferred promoter with or without an inducible system is cloned into a plant transformation vector comprising a maize CKI gene. Transformation is by standard methods and regenerated plants are selected and grown. Expression of the CKI gene from a male tissue-preferred promoter interferes with normal cell division and fertility. Fertility is tested by analysis of pollen and fertility testing through methods known in the art. Expression of the CKI gene from a female tissue-preferred promoter interferes with normal cell division and fertility. Fertility is tested by analysis of seed, embryos and fertility testing through methods known in the art.

Example 11

Identification of cDNA Clones and Expression

The CKI_B cDNA was truncated at the 5' during cloning such that it contained the conserved Cdc2 and Cyclin binding sites at the carboxy terminus of the protein, but did not have the start codon for the protein. After identifying CKI_C and aligning it with the *Arabidopsis* and Chenopodium CKIs obtained from Genbank, a conserved amino terminal motif was identified (MGKYMRK). This amino terminal motif turned up in another EST. After sequencing the 3' end of the cDNA it was confirmed to encode the same gene as the first CKI_B partial.

The protein-coding sequence from the second CKI_B clone was PCR amplified and subcloned into pRSET-B for production in *E. coli* under the control of the T7polymerase and fused to an oligohistidine stretch at the amino terminus. CKI_B protein was produced in BL21 cells and purified on Chelating sepharose fast flow (Pharmacia) under non-denaturing conditions according to standard protocols. Protein was eluted from the column and the presence of Histidine-tagged CKI_B confirmed using the anti-express antibody in SDS-PAGE immunoblot experiments. Protein extracts of maize immature ears was made by homogenizing the tissue in 2 ml/g TBS supplemented with 0.5% triton, 5 mM NaF, 1 mM Sodium OrthoVanadate, 1 mM PMSF, and 5 mM EDTA. Immature ear extract (2 ul) was mixed with a control or CKI_B, 10 ul Hepes ph 7.5 15 mM MgCl2 15 mM EGTA, and 2 ul of a 1:1:1 mixture of 2.5 mM ATP, 2.5 mMg32PATP and 2.5 mg.ml Histone H1 (calf, type IIIs Sigma) CKI_B was able to inhibit the majority of kinase activity present.

Many of the CKI_C clones were identified in kernel and endosperm libraries. The expression of CKI_C in kernels of multiple developmental stages can be analyzed. Northern blot and CKI_C RNA accumulation is developmentally regulated during kernel development. Message levels peak at 17 DAP (days after pollination), the period of maximal endoreduplication (See FIG. 1).

After identifying the conserved motif in CKI_C, CKI_B, and the Genbank accessions, CKI_D was identified. Unfortunately, the libraries in which CKI_D was identified were made using Sal I and NotI adapters. CKI_D contains a site for NotI within the coding sequence. This means that the CKI_D ESTs which contain the 5' end of CKI_D are encoded by cDNA clones that have been cut so the 3' end of the coding sequence and poly A tail were removed. Another clone provided the 3' end. CKI_D had a library distribution that includes a number of kernel libraries.

CKI_B, CKI_C and CKI_D have a unique and conserved domain SEQ ID NO: 7; MGKYMRK at the 5' end of the polypeptides. The nucleotide sequence encoding the polypeptide is SEQ ID NO: 8; ATG GGN AAR TAY ATG CGN AAR or SEQ ID NO: 9; ATG GGN AAR TAY ATG AGR AAR. The 3' region of the polypeptide contains a CDK binding region and/or cyclin binding domains;

CKI_B- SEQ ID NO: 10;
EFFAAAEAAQAKRFASKYNFDFVRGVPLDAGGRFEWAPVVSI;

CKI_C- SEQ ID NO: 11;
EYFAAEQRRQQQDFIDKYNFDPANDCPLPGRFEWVKLD;

CKI_D- SEQ ID NO: 12;
AQEIQEFFAAAEAAHAKRFASKYNFDFVRGVPLDAGRFEWTPGVSI.

CKI_B coding sequence is from 134-902 of Seq ID No. 1 encoding a polypeptide of 256 amino acids (Seq. ID No. 2) and having a poly A tail from approximately 1263-1290. CKI_C coding sequence is from 154-724 of Seq ID No. 3 encoding a polypeptide of 190 amino acids (Seq. ID No. 4) and having a poly A tail from approximately 1063-1079. CKI_D coding sequence is from 159-841 of Seq ID No. 5 encoding a polypeptide of 263 amino acids (Seq. ID No. 6) and having a poly A tail from approximately 1177-1201.

Degenerate oligos encoding the 5' conserved sequence and/or from the CDK binding region or elsewhere in the coding sequence are used to identify other CKI sequences via PCR, library screening or other molecular techniques.

Example 12

Cosuppression of CKI Expression Stimulates the Cell Cycle and Growth

Delivery of the CKI gene in an appropriate plant expression cassette is accomplished through numerous well-established methods for plant cells, including for example particle bombardment, sonication, PEG treatment or electroporation of protoplasts, electroporation of intact tissue, silica-fiber methods, microinjection or *Agrobacterium*-mediated transformation. As an alternative to conventional deliver of bacterial plasmids, introduction of a viral plasmid from which a CKI sequence is expressed could also be employed. While all the above methods can be used for cosuppression, physical methods of DNA delivery such as particle bombardment, sonication, PEG treatment or electroporation of protoplasts, electroporation of intact tissue, silica-fiber methods, or microinjection have an added advantage; in order to favor cosuppression in the resulting transformants, the absolute amount of CKI expression cassette is increased and/or the ratio of CKI expression cassette to selectable marker is raised. For example, to favor cosuppression in resulting transformants, particle mediated transformation is done as described below.

The ears are surface sterilized in 50% Chlorox bleach plus 0.5% Micro detergent for 20 minutes, and rinsed two times with sterile water. The immature embryos are excised and placed embryo axis side down (scutellum side up), 25 embryos per plate. These are cultured on 560 L medium 4 days prior to bombardment in the dark. Medium 560 L is Chu (N6) basal salts (Sigma C-1416) add 4 g per liter; Eriksson's Vitamin Mix; 1000× (Sigma-1511), add 1 ml/liter; Thiamine.HCl; final conc. 5 mg/l; Sucrose 20 g/l; 2,4-D; final conc. 1 mg/l; L-proline 2.88 g/l; silver nitrate; final conc. 8.5 mg/l; Gelrite; 2 g/l.

The day of bombardment, the embryos are transferred to 560 Y medium for 4 hours and are arranged within the 2.5-cm target zone. Medium 560Y is a high osmoticum medium (560L with high sucrose concentration)(560Y comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H₂O following adjustment to pH 5.8 with KOH); 2.0 g/l Gelrite (added after bringing to volume with D-I H$_2$O); and 8.5 mg/l silver nitrate (added after sterilizing the medium and cooling to room temperature).

A plasmid vector comprising a polynucleotide of the invention operably linked to the selected promoter is constructed. This plasmid DNA plus plasmid DNA containing a PAT~GFP selectable marker is precipitated onto 1.1 μm (average diameter) tungsten pellets using a CaCl$_2$ precipitation procedure as follows: 50 μl prepared tungsten particles (0.6 mg) in water, 1 μg total DNA (0.5 μg for each plasmid) in TrisEDTA buffer, 50 μl 2.5 M CaCl$_2$, 20 μl 0.1 M spermidine. Alternative heavy metal particles with tungsten, gold or platinum particles (0.6 to 1.1 μm) all being interchangeable in the protocol. To favor cosuppression, the amount of total DNA can be increased, preferably 2 to 10-fold although levels as high as 11 to 100-fold can be used. Alternatively, the amount of the plasmid containing the selectable marker can be maintained at the lower level and the amount of the CKI-expression plasmid be increased, preferably 2 to 10-fold, although levels as high as 11 to 100-fold can be used.

Each reagent is added sequentially to the tungsten particle suspension. The final mixture is sonicated briefly. After the precipitation period, the tubes are centrifuged briefly, liquid removed, washed with 250 ml 100% ethanol, and centrifuged again for 30 seconds. Again the liquid is removed, and 30 μl 100% ethanol is added to the final tungsten particle pellet. For particle gun bombardment, the tungsten/DNA particles are briefly sonicated and 5 μl spotted onto the center of each macrocarrier and allowed to dry about 2 minutes before bombardment.

The sample plates are bombarded at a distance of 8 cm from the stopping screen to the tissue, using a Dupont biolistics helium particle gun. All samples receive a single shot at 650 PSI, with a total of ten aliquots taken from each tube of prepared particles/DNA.

Four to twelve hours post bombardment, the embryos are moved to 560P (a low osmoticum callus initiation medium similar to 560L but with lower silver nitrate (see Ser. No. 09/425,510, which is incorporated by reference), for 3-7 days, then transferred to 560R selection medium, an N6 based medium similar to 560P containing 3 mg/liter Bialaphos, and subcultured every 2 weeks. Multicellular GFP cell clusters become visible after two weeks and their numbers are periodically recorded. After approximately 10 weeks of selection, selection-resistant GFP positive callus clones are sampled for PCR and activity of the polynucleotide of interest. Positive lines are transferred to 288J medium, an MS-based medium with lower sucrose and hormone levels, to initiate plant regeneration (Ser. No. 09/907,411 incorporated by reference). Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic™ 600 pots (1.6 gallon) and grown to maturity. Plants are monitored for expression of the polynucleotide of interest.

The result of ZmCKI (*Zea mays* CKI) cosuppression will be to stimulate the G1/S transition and hence cell division, providing the optimal cellular environment for integration of introduced genes. However, beyond the transient effects on transgenic integration, continued cosuppression of the ZmCKI will trigger a tissue culture response (cell divisions) in genotypes that typically do not respond to conventional culture techniques, or stimulate growth of transgenic tissue beyond the normal rates observed in wild-type (non-transgenic) tissues. To demonstrate this, the CKI gene is cloned into a cassette with a constitutive promoter (i.e. either a strong maize promoter such as the ubiquitin promoter including the first ubiquitin intron, or a weak constitutive promoter such as nos). Either particle-mediated DNA delivery or *Agrobacterium*-mediated delivery are used to introduce the UBI::ZmCKI::pinII-containing plasmid along with a UBI:PAT~GFP::pinII-containing plasmid into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids, and within 1-7 days the embryos are moved onto culture medium containing 3 mg/l of the selective agent bialaphos. Embryos, and later callus, are transferred to fresh selection plates every 2 weeks.

After 6-8 weeks, transformed calli are recovered. In treatments where both the PAT~GFP fusion and the CKI gene have been transformed into immature embryos, a higher number of growing calli are recovered on the selective medium and callus growth is stimulated (relative to treatments with the bar gene alone). When the CKI gene is introduced without any additional selectable marker, transgenic calli can be identified by their ability to grow more rapidly than surrounding wild-type (non-transformed) tissues. Transgenic callus can be verified using PCR and Southern analysis. Northern analysis can also be used to verify which calli are expressing the bar gene, and which are exhibiting cosuppression of the CKI gene.

Example 13

Cosuppression of CKI Expression Using Tissue-Specific or Cell-Specific Promoters Provides a Differential Growth Advantage A ZmCKI gene is introduced in a manner that favors cosuppression. In addition, the transgene is expressed using tissue-specific or cell-specific promoters, resulting in tissue-specific or cell-specific stimulation of cell cycle progression in the expressing tissues or cells. For example, using a seed-specific promoter will stimulate cell division rate and result in increased seed biomass. Alternatively, driving ZmCKI expression with a strongly-expressed, early, tassel-specific promoter will enhance development of this entire reproductive structure.

Expression of ZmCKI genes in other cell types and/or at different stages of development will similarly stimulate cell division rates. Root-specific or root-preferred expression of ZmCKI will result in larger roots and faster growth (i.e. more biomass accumulation).

What is claimed is:

1. An isolated nucleic acid comprising the polynucleotide set forth in SEQ ID NO: 1.

2. The isolated nucleic acid of claim 1 adducted to a second nucleic acid sequence encoding a DNA-binding domain.

3. A vector comprising at least one nucleic acid of claim 1.

4. An expression cassette comprising at least one nucleic acid of claim 1 operably linked to a promoter.

5. A host cell containing at least one expression cassette of claim 4.

6. The host cell of claim 5, wherein said host cell comprises a bacterium, yeast cell, insect cell or plant cell.

7. A transgenic plant comprising at least one expression cassette of claim 4.

8. The transgenic plant of claim 7, wherein the plant is corn, soybean, sunflower, sorghum, canola, wheat, alfalfa, cotton, rice, barley, oil-seed *Brassica* and millet.

9. A transgenic seed comprising at least one expression cassette of claim 4.

10. The transgenic seed of claim 9, wherein the transgenic seed is from corn, soybean, sunflower, sorghum, canola, wheat, alfalfa, cotton, rice, barley, oil-seed *Brassica* and millet.

11. An isolated polynucleotide that encodes the polypeptide of SEQ ID NO: 2.

12. An isolated polynucleotide which is fully complementary to a polynucleotide of claim 11.

13. An expression cassette comprising at least one nucleic acid of claim 11 operably linked to a promoter.

14. A host cell containing at least one expression cassette of claim 13.

15. The host cell of claim 14, wherein said host cell comprises a bacterium, yeast cell, insect cell or plant cell.

16. A transgenic plant comprising at least one expression cassette of claim 13.

17. The transgenic plant of claim 16, wherein the plant is corn, soybean, sunflower, sorghum, canola, wheat, alfalfa, cotton, rice, barley, oil-seed *Brassica* and millet.

18. A transgenic seed comprising at least one expression cassette of claim 13.

19. The transgenic seed of claim 18, wherein the transgenic seed is from corn, soybean, sunflower, sorghum, canola, wheat, alfalfa, cotton, rice, barley, oil-seed *Brassica* and millet.

* * * * *

SEQUENCE LISTING

<160> NUMBER OF SEQ ID NOS: 6

<210> SEQ ID NO 1
<211> LENGTH: 1372
<212> TYPE: DNA
<213> ORGANISM: zea mays
<220> FEATURE:
<221> NAME/KEY: CDS
<222> LOCATION: (134)...(902)

<400> SEQUENCE: 1

```
cccacgcgtc cggacgcaag cggctgcagg cagcagcgcc gcgcaggcgt tgtggcctgt       60
gggagaggaa aaagagaaag aggaaccggc caagacaagc aagcgagagg ccagggccgc      120
ggcgttgcgt cag atg ggg aag tac atg cgc aag tgc agg ggc gcc gca        169
            Met Gly Lys Tyr Met Arg Lys Cys Arg Gly Ala Ala
                 1               5                  10 ggc gcg gag gtc gcc gcc gtc gag gtt acg cag gtc gtc ggc gtc cgg       217
Gly Ala Glu Val Ala Ala Val Glu Val Thr Gln Val Val Gly Val Arg
         15                  20                  25 acg agg tcc agg tcc gcg gcg gcg acc ggc ggt gtc gcg aag gtc gcc       265
Thr Arg Ser Arg Ser Ala Ala Ala Thr Gly Gly Val Ala Lys Val Ala
 30                  35                  40 ccg agg agg aag agg gcg ccg gcg ggg gag cct gct gcc gcc gtg agc       313
Pro Arg Arg Lys Arg Ala Pro Ala Gly Glu Pro Ala Ala Ala Val Ser
 45                  50                  55                  60 gct ggt ggg gac ggc gga agc tgc tac atc cac ctg cgt agc cgc atg       361
Ala Gly Gly Asp Gly Gly Ser Cys Tyr Ile His Leu Arg Ser Arg Met
                 65                  70                  75 ctg ttc atg gca ccg cct cag ccg cag ccg tcg gtt gac tcg gtt ccg       409
Leu Phe Met Ala Pro Pro Gln Pro Gln Pro Ser Val Asp Ser Val Pro
         80                  85                  90 acc ccg gtg gag gct gct gat ggc gct gca gga cag cag ggc gcg gcg       457
Thr Pro Val Glu Ala Ala Asp Gly Ala Ala Gly Gln Gln Gly Ala Ala
     95                 100                 105 ctc gcg gcc ggg ctc tcg cgt tgc tcc agc acg gcg tcg tcg gtg aac       505
Leu Ala Ala Gly Leu Ser Arg Cys Ser Ser Thr Ala Ser Ser Val Asn
110                 115                 120 ttg ggc ttg ggg ggt cag cgc ggg agc cac acc tgc cgc tcc tac gac       553
Leu Gly Leu Gly Gly Gln Arg Gly Ser His Thr Cys Arg Ser Tyr Asp
125                 130                 135                 140 gct gca gag gct ggc ggg gat cac gtc ctg gtg gat gtc tcg gcg gcg       601
Ala Ala Glu Ala Gly Gly Asp His Val Leu Val Asp Val Ser Ala Ala
                145                 150                 155 agc aac tcc ggg agc ggc cca gac cgc gag agg cga gag acg acg cca       649
Ser Asn Ser Gly Ser Gly Pro Asp Arg Glu Arg Arg Glu Thr Thr Pro
            160                 165                 170 tcg agc cgg gcg cac ggc gag ctc agc gat ctg gag tcg gat ctg gcg       697
Ser Ser Arg Ala His Gly Glu Leu Ser Asp Leu Glu Ser Asp Leu Ala
        175                 180                 185 ggg cac aag act ggc ccg tcg cta ccg gcg gca acg ccg gct gcg gag       745
Gly His Lys Thr Gly Pro Ser Leu Pro Ala Ala Thr Pro Ala Ala Glu
    190                 195                 200 ctg atc gtg ccg cca gca cac gag atc cag gag ttc ttc gcc gcc gcc       793
Leu Ile Val Pro Pro Ala His Glu Ile Gln Glu Phe Phe Ala Ala Ala
205                 210                 215                 220 gag gcg gcc cag gcc aag cgc ttt gct tcc aag tac aac ttc gac ttc       841
Glu Ala Ala Gln Ala Lys Arg Phe Ala Ser Lys Tyr Asn Phe Asp Phe
                225                 230                 235
```

```
gtc cgc ggc gtg ccc ctc gac gcc ggc ggc cgg ttc gag tgg gcg ccg    889
Val Arg Gly Val Pro Leu Asp Ala Gly Gly Arg Phe Glu Trp Ala Pro
            240                 245                 250 gtg gtc agc atc t gaagcgagcg tgcgtccggt gcaaggtgaa gctagaaaga      942
Val Val Ser Ile
        255 gaaaagatgc cccccccccc cccccccaac aaacataacg gagaagagaa aaaccaaaca 1002 attaagcagc tttatatagc ctaagctaac caccaccatt catctcgtcc aaatgcatgc 1062 cttgcttttc tctggagcta gcaggagcgt agttattatt tagtactact ttacttattc 1122 agaggttatc ttgaccccga tagatcaatc cgcttactgt gtaatttctc tcatgcatct 1182 cttagatgga gtttaatcgt cttaatttat tactgtacag cagcttgstt ggcttgcaaa 1242 gaaagatctg gtttgtctca aaaaaaaaaa aaaaaaaaaa aaaaaagggg cggccgctct 1302 agaggatcca agcttacgta cgcgtgcatg cgacgtcata gctcttctat agtgtcacct 1362 aaattcattc                                                        1372

<210> SEQ ID NO 2
<211> LENGTH: 256
<212> TYPE: PRT
<213> ORGANISM: zea mays
<220> FEATURE:
<221> NAME/KEY: VARIANT
<222> LOCATION: (1)...(256)
<223> OTHER INFORMATION: Xaa = Any Amino Acid

<400> SEQUENCE: 2

Met Gly Lys Tyr Met Arg Lys Cys Arg Gly Ala Ala Gly Ala Glu Val
1               5                   10                  15

Ala Ala Val Glu Val Thr Gln Val Val Gly Val Arg Thr Arg Ser Arg
            20                  25                  30

Ser Ala Ala Thr Gly Gly Val Ala Lys Val Ala Pro Arg Arg Lys
        35                  40                  45

Arg Ala Pro Ala Gly Glu Pro Ala Ala Val Ser Ala Gly Gly Asp
    50                  55                  60

Gly Gly Ser Cys Tyr Ile His Leu Arg Ser Arg Met Leu Phe Met Ala
65                  70                  75                  80

Pro Pro Gln Pro Gln Pro Ser Val Asp Ser Val Pro Thr Pro Val Glu
                85                  90                  95

Ala Ala Asp Gly Ala Ala Gly Gln Gln Gly Ala Ala Leu Ala Ala Gly
            100                 105                 110

Leu Ser Arg Cys Ser Ser Thr Ala Ser Ser Val Asn Leu Gly Leu Gly
        115                 120                 125

Gly Gln Arg Gly Ser His Thr Cys Arg Ser Tyr Asp Ala Ala Glu Ala
    130                 135                 140

Gly Gly Asp His Val Leu Val Asp Val Ser Ala Ala Ser Asn Ser Gly
145                 150                 155                 160

Ser Gly Pro Asp Arg Glu Arg Glu Thr Thr Pro Ser Ser Arg Ala
                165                 170                 175

His Gly Glu Leu Ser Asp Leu Glu Ser Asp Leu Ala Gly His Lys Thr
            180                 185                 190

Gly Pro Ser Leu Pro Ala Thr Pro Ala Ala Glu Leu Ile Val Pro
        195                 200                 205

Pro Ala His Glu Ile Gln Glu Phe Phe Ala Ala Glu Ala Ala Gln
    210                 215                 220

Ala Lys Arg Phe Ala Ser Lys Tyr Asn Phe Asp Phe Val Arg Gly Val
```

```
                    225                 230                 235                 240

Pro Leu Asp Ala Gly Gly Arg Phe Glu Trp Ala Pro Val Val Ser Ile
                    245                 250                 255

<210> SEQ ID NO 3
<211> LENGTH: 1089
<212> TYPE: DNA
<213> ORGANISM: zea mays
<220> FEATURE:
<221> NAME/KEY: CDS
<222> LOCATION: (154)...(724)

<400> SEQUENCE: 3
cccacgcgtc cgccctcctg tgtacaccac tcccgccccg cctaccattt tatccccgcc      60
tctcctggcc tctgccgccc cgtcgcacag aatcgcttgg tgcaccctgc gagggcctcc     120
tcgaaaccct agcttgccca gcccctccgg gcc atg ggc aag tac atg cgc aag     174
                                    Met Gly Lys Tyr Met Arg Lys
                                     1               5 gcc aag gct tcc agc gag gtt gtc atc atg gat gtc gcc gcc gct ccg     222
Ala Lys Ala Ser Ser Glu Val Val Ile Met Asp Val Ala Ala Ala Pro
           10                  15                  20 ctc gga gtc cgc acc cga gcg cgc gcc ctc gcg ctg cag cgt ctg cag     270
Leu Gly Val Arg Thr Arg Ala Arg Ala Leu Ala Leu Gln Arg Leu Gln
       25                  30                  35 gag cag cag acg cag tgg gag gaa ggt gct ggc ggc gag tac ctg gag     318
Glu Gln Gln Thr Gln Trp Glu Glu Gly Ala Gly Gly Glu Tyr Leu Glu
   40                  45                  50                  55 cta agg aac cgg agg ctc gag aag ctg ccg ccg ccg gcg acc acg         366
Leu Arg Asn Arg Arg Leu Glu Lys Leu Pro Pro Pro Ala Thr Thr
                   60                  65                  70 agg agg tcg ggc ggg agg aaa gcg gca gcc gag gcc gcc gca act aag     414
Arg Arg Ser Gly Gly Arg Lys Ala Ala Ala Glu Ala Ala Ala Thr Lys
               75                  80                  85 gag gct gag gcg tcg tac ggg gag aac atg ctc gag ttg gag gcc atg     462
Glu Ala Glu Ala Ser Tyr Gly Glu Asn Met Leu Glu Leu Glu Ala Met
           90                  95                 100 gag agg att acc agg gag acg acg cct tgc agc ttg att aac acc cag     510
Glu Arg Ile Thr Arg Glu Thr Thr Pro Cys Ser Leu Ile Asn Thr Gln
       105                 110                 115 atg act agc act cct ggg tcc acg aga tcc agc cac tct tgc cac cgc     558
Met Thr Ser Thr Pro Gly Ser Thr Arg Ser Ser His Ser Cys His Arg
120                 125                 130                 135 agg gtg aac gct cct ccg gtg cac gcc gtc cca agt tcg agg gag atg     606
Arg Val Asn Ala Pro Pro Val His Ala Val Pro Ser Ser Arg Glu Met
                   140                 145                 150 aat gag tac ttc gct gcc gaa cag cga cgc caa caa cag gat ttc att     654
Asn Glu Tyr Phe Ala Ala Glu Gln Arg Arg Gln Gln Gln Asp Phe Ile
               155                 160                 165 gac aag tac aac ttc gat cct gca aac gac tgc cct ctc cca ggc agg     702
Asp Lys Tyr Asn Phe Asp Pro Ala Asn Asp Cys Pro Leu Pro Gly Arg
           170                 175                 180 ttt gag tgg gtg aag cta gac t gatggattca gagggacgag agagcagcag      754
Phe Glu Trp Val Lys Leu Asp
       185                 190 gcatggaatg gaatggaact cacccccgc tccctccaca ccaccccagc gttgtggcag    814
aggcgcatac cgtcgtgtta gcttcgtttc tgctgtaaaa aaaaacttag tgttttagca    874
tgtagcctta attggtcgtg tgttacagta cagaactgat gctgagttac aacaccctga    934
tctggtcttg atctgatccc tcaactccaa tgtaaccctt aacagctcat tctgtaagga    994
```

```
acctgtcacc ctgttacctg ttgctgaact aatgaagtag agctagataa tgacgtttta    1054
tcgtagttaa aaaaaaaaaa aaaaagggcg gccgc                                1089

<210> SEQ ID NO 4
<211> LENGTH: 190
<212> TYPE: PRT
<213> ORGANISM: zea mays

<400> SEQUENCE: 4

Met Gly Lys Tyr Met Arg Lys Ala Lys Ala Ser Ser Glu Val Val Ile
 1               5                  10                  15

Met Asp Val Ala Ala Ala Pro Leu Gly Val Arg Thr Arg Ala Arg Ala
                20                  25                  30

Leu Ala Leu Gln Arg Leu Gln Glu Gln Gln Thr Gln Trp Glu Glu Gly
            35                  40                  45

Ala Gly Gly Glu Tyr Leu Glu Leu Arg Asn Arg Leu Glu Lys Leu
        50                  55                  60

Pro Pro Pro Pro Ala Thr Thr Arg Arg Ser Gly Gly Arg Lys Ala Ala
65                  70                  75                  80

Ala Glu Ala Ala Ala Thr Lys Glu Ala Glu Ala Ser Tyr Gly Glu Asn
                85                  90                  95

Met Leu Glu Leu Glu Ala Met Glu Arg Ile Thr Arg Glu Thr Thr Pro
            100                 105                 110

Cys Ser Leu Ile Asn Thr Gln Met Thr Ser Thr Pro Gly Ser Thr Arg
        115                 120                 125

Ser Ser His Ser Cys His Arg Arg Val Asn Ala Pro Pro Val His Ala
    130                 135                 140

Val Pro Ser Ser Arg Glu Met Asn Glu Tyr Phe Ala Ala Glu Gln Arg
145                 150                 155                 160

Arg Gln Gln Gln Asp Phe Ile Asp Lys Tyr Asn Phe Asp Pro Ala Asn
                165                 170                 175

Asp Cys Pro Leu Pro Gly Arg Phe Glu Trp Val Lys Leu Asp
            180                 185                 190

<210> SEQ ID NO 5
<211> LENGTH: 841
<212> TYPE: DNA
<213> ORGANISM: zea mays
<220> FEATURE:
<221> NAME/KEY: CDS
<222> LOCATION: (159)...(841)
<223> OTHER INFORMATION: r= g or a

<400> SEQUENCE: 5
cccacgcgtc cgagtagaat ccaaagcgca agcggctgca gcctgcaggc agcgccgcgc    60
aggcgtggga gtggccgagt gggagtggga gtgaaaaaga ggaaccggcc aagagaagca   120
agcgagaaga aggcagtgct gcggcggcgt tccgtaag atg ggg aag tac atg cgc   176
                                          Met Gly Lys Tyr Met Arg
                                           1               5 aag cgc agg ggg gcc gcg ggc gag ggg gtg gcc gca gtc gag gtc tcg   224
Lys Arg Arg Gly Ala Ala Gly Glu Gly Val Ala Ala Val Glu Val Ser
            10                  15                  20 cag gtc gtc ggc gtc cgg acg agg tcc agg tcc gcg gcg gcg acc ggc   272
Gln Val Val Gly Val Arg Thr Arg Ser Arg Ser Ala Ala Ala Thr Gly
        25                  30                  35 ggc ggt gtc gcg aag gtc gct ccg ccg agg agg aag aag gcg ctg ctg   320
Gly Gly Val Ala Lys Val Ala Pro Pro Arg Arg Lys Lys Ala Leu Leu
    40                  45                  50
```

```
                40                  45                  50
ccc gcc gcg aac gtg acg acg tcg ggg gag cct ggt gcc gtg ggc gct        368
Pro Ala Ala Asn Val Thr Thr Ser Gly Glu Pro Gly Ala Val Gly Ala
 55                  60                  65                  70 ggt ggt ggg gac ggc gga agc tgc tgc tac atc cac ctg cgg agc cgc        416
Gly Gly Gly Asp Gly Gly Ser Cys Cys Tyr Ile His Leu Arg Ser Arg
             75                  80                  85 atg ctg ttc atg gca gca cct cag cag caa ccg tcg gcg gct ctg acg        464
Met Leu Phe Met Ala Ala Pro Gln Gln Gln Pro Ser Ala Ala Leu Thr
             90                  95                 100 ccg gtg gag gct gct ggt gcg gca car caa ggc ggg gtg gtg gcg ctc        512
Pro Val Glu Ala Ala Gly Ala Ala Xaa Gln Gly Gly Val Val Ala Leu
        105                 110                 115 gcg gct ggc ctc tcg cgt tgc tcc agc acg gcg tcg tcg gtg gac gtc        560
Ala Ala Gly Leu Ser Arg Cys Ser Ser Thr Ala Ser Ser Val Asp Val
        120                 125                 130 ggg ggc cac gcc tgc cgc tcc gac gct gcg cct gcg gag gtt gac ggg        608
Gly Gly His Ala Cys Arg Ser Asp Ala Ala Pro Ala Glu Val Asp Gly
135                 140                 145                 150 gat cac gtc ccg gat gtc gtc acc gcg agc aac tcg ggg agc gtc ccg        656
Asp His Val Pro Asp Val Val Thr Ala Ser Asn Ser Gly Ser Val Pro
                155                 160                 165 gac cgc gag agg aga gag acg acg cca tcg tcg agc cgg gcg cac ggc        704
Asp Arg Glu Arg Arg Glu Thr Thr Pro Ser Ser Ser Arg Ala His Gly
        170                 175                 180 ggc gag ctc agc gat ctg gag tcg gat ctg gtg ggg cgg cag aag act        752
Gly Glu Leu Ser Asp Leu Glu Ser Asp Leu Val Gly Arg Gln Lys Thr
        185                 190                 195 ggc tgc tcg tcg tcg ccg gcg aca aca aca tcg gct gcg gag ctg atc        800
Gly Cys Ser Ser Ser Pro Ala Thr Thr Thr Ser Ala Ala Glu Leu Ile
200                 205                 210 gtg ccg cca gca cag gag atc cag gaa ttc ttc gcg gcc gc                 841
Val Pro Pro Ala Gln Glu Ile Gln Glu Phe Phe Ala Ala
215                 220                 225

<210> SEQ ID NO 6
<211> LENGTH: 227
<212> TYPE: PRT
<213> ORGANISM: zea mays
<220> FEATURE:
<221> NAME/KEY: VARIANT
<222> LOCATION: (1)...(227)
<223> OTHER INFORMATION: Xaa = Any Amino Acid

<400> SEQUENCE: 6

Met Gly Lys Tyr Met Arg Lys Arg Arg Gly Ala Ala Gly Glu Gly Val
  1               5                  10                  15

Ala Ala Val Glu Val Ser Gln Val Val Gly Val Arg Thr Arg Ser Arg
                 20                  25                  30

Ser Ala Ala Ala Thr Gly Gly Val Ala Lys Val Ala Pro Pro Arg
             35                  40                  45

Arg Lys Lys Ala Leu Leu Pro Ala Ala Asn Val Thr Thr Ser Gly Glu
 50                  55                  60

Pro Gly Ala Val Gly Ala Gly Gly Asp Gly Gly Ser Cys Cys Tyr
 65                  70                  75                  80

Ile His Leu Arg Ser Arg Met Leu Phe Met Ala Ala Pro Gln Gln Gln
                 85                  90                  95

Pro Ser Ala Ala Leu Thr Pro Val Glu Ala Ala Gly Ala Ala Xaa Gln
            100                 105                 110
```

-continued

```
Gly Gly Val Val Ala Leu Ala Ala Gly Leu Ser Arg Cys Ser Ser Thr
        115                 120                 125

Ala Ser Ser Val Asp Val Gly Gly His Ala Cys Arg Ser Asp Ala Ala
        130                 135                 140

Pro Ala Glu Val Asp Gly Asp His Val Pro Asp Val Val Thr Ala Ser
145                 150                 155                 160

Asn Ser Gly Ser Val Pro Asp Arg Glu Arg Arg Glu Thr Thr Pro Ser
                165                 170                 175

Ser Ser Arg Ala His Gly Gly Glu Leu Ser Asp Leu Glu Ser Asp Leu
            180                 185                 190

Val Gly Arg Gln Lys Thr Gly Cys Ser Ser Ser Pro Ala Thr Thr Thr
        195                 200                 205

Ser Ala Ala Glu Leu Ile Val Pro Pro Ala Gln Glu Ile Gln Glu Phe
    210                 215                 220

Phe Ala Ala
225
```